United States Patent [19]

Rogers

[11] 4,200,635
[45] Apr. 29, 1980

[54] ANTIBACTERIALLY ACTIVE AMIDES

[75] Inventor: Norman H. Rogers, Rudgwick, England

[73] Assignee: Beecham Group Limited, Great Britain

[21] Appl. No.: 957,054

[22] Filed: Nov. 3, 1978

[30] Foreign Application Priority Data

Nov. 5, 1977 [GB] United Kingdom ............... 46120/77

[51] Int. Cl.$^2$ ............................................. C07D 407/06
[52] U.S. Cl. ......................... 424/248.57; 260/345.7 R; 424/267; 424/274; 424/283; 542/421; 542/438
[58] Field of Search ........... 424/283, 274, 267, 248.57; 260/345.7 R; 542/438, 421

[56] References Cited

U.S. PATENT DOCUMENTS 4,102,901  7/1978  Luk et al. .............................. 424/283
4,102,904  7/1978  Luk et al. .............................. 424/283

FOREIGN PATENT DOCUMENTS 2706542  8/1977  Fed. Rep. of Germany .

Primary Examiner—Arthur P. Demers
Attorney, Agent, or Firm—Jacobs & Jacobs

[57] ABSTRACT

Carboxylic acid amides of formula (II):

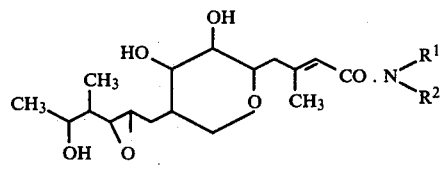

where $R^1$ and $R^2$ represent a variety of hydrocarbon or heterocyclic groups, possess antibacterial activity and antimycoplasmal activity and are therefore of value in the treatment of human and veterinary bacterial and mycoplasmal infections.

6 Claims, No Drawings

ANTIBACTERIALLY ACTIVE AMIDES

This invention relates to antibacterial compounds and in particular to a class of amides which have anti-bacterial activity against certain Gram-positive and Gram-negative organisms, in particular *Haemophilis influenzae* and also possess good antimycoplasmal activity. The compounds are therefore of value in the treatment of veterinary bacterial infections and of particular value in humans in the treatment of bronchitis and venereal disease.

Our British cognate patent application number 24712/75, 40472/76 and 8647/77 discloses an acid of formula (I):

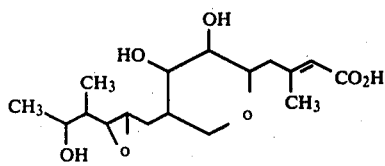

which will be referred to herein as 'monic acid A'. Although this compound does not appear to have anti-bacterial activity, esters thereof do possess antibacterial activity, as disclosed in our British cognate application number 23536/77, 23548/77, 23549/77. It is believed that monic acid A has the absolute stereochemistry as shown in formula (IA):

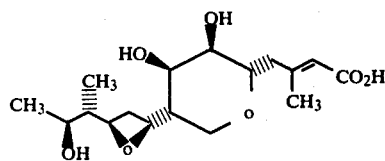

It has now been found that certain amides of monic acid A also possess anti-bacterial activity. Accordingly the present invention provides a carboxylic acid amide of formula (II):

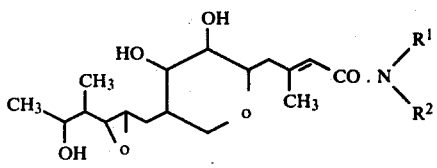

wherein $R^1$ and $R^2$ are the same or different and each represent (a) hydrogen, or (b) $C_{1-20}$ alkyl, $C_{2-8}$ alkenyl, either of which may be optionally substituted with $C_{3-7}$ cycloalkyl, halogen, carboxy, $C_{1-6}$ alkoxycarbonyl, carbamyl, aryl, heterocyclyl, hydroxy, $C_{1-6}$ alkanoyloxy, amino, mono- or di-($C_{1-6}$) alkylamino; or (c) $C_{3-7}$ cycloalkyl optionally substituted with $C_{1-6}$ alkyl; or (d) aryl; or (e) heterocyclyl; or (f) $R^1$ and $R^2$ together with the nitrogen atom to which they are attached represent a $C_{5-7}$ heterocyclic ring.

The term 'aryl' includes phenyl, and naphthyl optionally substituted with up to five halogen, $C_{1-6}$ alkyl, $C_{1-6}$ alkoxy, halo($C_{1-6}$) alkyl, hydroxy, amino, carboxy, $C_{1-6}$ alkoxycarbonyl, or $C_{1-6}$ alkoxycarbonyl ($C_{1-6}$) alkyl groups.

The term 'heterocyclyl' includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo($C_{1-6}$) alkyl, hydroxy, amino, carboxy, $C_{1-6}$ alkoxycarbonyl, $C_{1-6}$ alkoxy-carbonyl($C_{1-6}$)alkyl, aryl or oxo groups.

One suitable substituted alkyl group for the group $R^1$ or $R^2$ has the formula (III):

$$-(CH_2)_nCO_2R^3 \qquad (III)$$

wherein n is an interger from 1 to 20 and $R^3$ is hydrogen or a pharmaceutically acceptable salt-forming ion or $C_{1-6}$ alkyl.

Thus the group $R^1$ or $R^2$ in compound (II) may be for example $C_{1-6}$ alkyl, in particular, methyl, ethyl n- or iso-propyl, n-, sec-, iso- or tert-butyl; halo($C_{1-6}$)-alkyl such as trifluoromethyl, 2-chloroethyl, 2,2,2-trichloroethyl; aminoalkyl groups such as aminoethyl, 2-aminoethyl; hydroxymethyl, 2-hydroxyethyl; phenyl; substituted phenyl; a benzyl group; or a group of formula (III) wherein n is an integer from 1 to 10; or together with the nitrogen atom to which they are attached form pyrrolidinyl, piperidinyl, or morpholinyl.

Other specific examples of the group $R^1$ or $R^2$ include: $C_{7-20}$ alkyl groups such as heptyl, octyl, nonyl, decyl and dodecyl; cyclopropyl, cyclopropylmethyl, cyclopentyl, 3-methoxycarbonylpropyl, 4-methoxycarbonyl-n-butyl, 5-methoxycarbonyl-n-pentyl, 6-methoxycarbonyl-n hexyl, 7-methoxycarbonyl-n-heptyl, 10-methoxycarbonyldecyl, carbamoylmethyl, benzyl, 2,4,6-trichlorophenyl, pentachlorophenyl, o-, m or p-methylphenyl, o-, m- or p-methoxycarbonylphenyl, 2-, 3- or 4-pyridyl, prop-2-enyl, 2-dialkylaminoethyl, or 3-methoxycarbonylprop-2-enyl.

Another class of amides of the present invention are those in which $R^1$ is hydrogen and $R^2$ is such that $R^2NH_2$ represents an amino-acid preferably a naturally occurring amino acid. For example if $R^2NH_2$ represents glycine, the amide of this invention is the compound of formula (II) in which $R^1$ is hydrogen and $R^2$ is —$CH_2CO_2H$.

Preferred amides of monic acid A of this invention are those in which $R^1$ is hydrogen or $C_1$ to $C_6$ alkyl and $R^2$ is hydrogen, $C_1$ to $C_6$ alkyl, $C_1$ to $C_6$ alkenyl, or a group of formula (III) above, or $R^1$ and $R^2$ together with the nitrogen atom to which they are attached form a pyrrolidinyl, piperidinyl or morpholinyl ring.

Specific compounds of this invention include the following amides of monic acid A:
primary amide ($R^1=R^2=H$);
N-methylamide ($R^1=H$, $R^2=CH_3$);
methoxycarbonylmethyl amide ($R^1=H$, $R^2=-CH_2CO_2CH_3$);
N,N-dimethylamide ($R^1=R^2=CH_3$);
5-ethoxycarbonylpentylamide ($R^1=H$, $R^2=-(CH_2)_5CO_2-C_2H_5$);
N-morpholinylamide

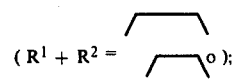

8-methoxycarbonyloctylamide ($R^1=H$, $R^2=-(CH_2)_8CO_2CH_3$);
allylamide ($R^1=H$, $R^2=-CH_2-CH=CH_2$);
5-methoxycarbonylpentylamide ($R^1=H$, $R^2=-(CH_2)_5CO_2-CH_3$);

methoxycarbonylethyl amide ($R^1$=H, $R^2$=—$(CH_2)_2CO_2CH_3$).

The compounds of formula (II) may be prepared from monic acid A of formula (I) by conventional techniques for producing amides of carboxylic acids.

Suitably a reactive derivative of monic acid A is reacted with an amine $R^1R^2$.NH. Preferred reactive derivatives include mixed anhydrides formed for example with isobutylchoroformate, ethyl chloroformate, pivaloyl chloride and other reagents for generating mixed anhydrides. Alternative reactive derivatives of acid (I) are activated esters such as esters with cyanomethanol, p-nitrophenol, 2,4-dinitrophenol, thiophenol, halophenol, including pentachlorophenol, monomethoxyphenol or 8-hydroxyquinoline; or amides such as N-acylsacchrins or N-acylphthalimides; or an alkylidene iminoester prepared by reaction of the acid (I) with an oxime.

Some activated esters, for example the ester formed with 1-hydroxybenztriazole or N-hydroxysuccinimide, may be prepared in situ by the reaction of the acid with the appropriate hydroxy compound in the presence of a carbodiimide, for example N,N-diethyl, dipropyl- or diisopropylcarbodiimide, N,N'-di-cyclohexylcarbodiimide, or N-ethyl-N'- -dimethylaminopropylcarbodiimide; a suitable carbonyl compound, for example N,N'-carbonyldiimidazole or N,N'-carbonylditriazole.

Suitable solvents for the process of this invention include inert aprotic solvents, such as tetrahydrofuran, methylene dichloride, N,N-dimethylacetamide. The reaction is generally carried out at low temperature for example $-25°$ C. to $0°$ C., preferably at about $-10°$ C.

The antibiotic compounds according to the invention may be formulated for administration in any convenient way for use in human or veterinary medicine, by analogy with other antibiotics, and the invention therefore includes within its scope a pharmaceutical or veterinary composition comprising a compound of formula (II) above together with a pharmaceutical or veterinary carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-prollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; nonaqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa, butter or other glyceride.

For patenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day, depending on the route and frequency of administration.

The following Examples illustrate the present invention.

EXAMPLE 1

Primary amide of monic acid A

Monic acid (1.032 g; 3 mM) was dissolved in dry tetrahydrofuran (50 ml) and stirred at $-20°$ C. for 20 minutes with triethylamine (420 $\mu$l; 3 mM) and isobutylchloroformate (390 $\mu$l; 3 mM). Ammonia solution (specific gravity 0.88; approximately 35%; 340 $\mu$l; approximately 6 mM) was then added and the solution stirred at $0°$ C. for two hours and room temperature for 16 hours. The white precipitate was then filtered and the filtrate evaporated to dryness at reduced pressure. The residual oil was then partitioned between ethyl acetate and saturated sodium bicarbonate solution. The organic solution was dried over magnesium sulphate. However, thin layer chromatography revealed that the product had also dissolved in the aqueous phase. Hence, the aqueous solution was evaporated to dryness at reduced pressure, digested in methanol and filtered. The filtrate was combined with the ethyl acetate solution and the solvent was removed at reduced pressure to yield a colourless oil (0.990 g). This oil was purified by preparative thin layer chromatography on three 20 cm $\times$ 20 cm $\times$ 2 mm silica plates, eluting with 25% methanol/chloroform. The pure amide was obtained as a colourless oil (0.518 g; 52%). $[\alpha]_D^{20}$ (c 1.0, $CH_3OH$) $-13.8°$, $\lambda_{max}$ (EtOH) 219 nm ($\epsilon_m$ 13,100), $\nu_{max}$(CHBr$_3$) 3300, 2500, 1660, 1630 and 1610 cm$^{-1}$, $\delta_H$(CD$_3$OD) 5.73 (1H, s, C$\underline{H}$=C); 2.10 (3H, s,

1.18 (3H, d, J=6.0 Hz, C$\underline{H}_3$-14); 0.92 (3H, d, J=7.0 Hz, C$\underline{H}_3$-17), $\delta_C$ (CD$_3$OD) 172.0, 153.2, 120.5, 76.1, 71.5, 70.6, 69.9, 66.2, 61.2, 56.8, 43.5, 41.4, 23.8, 20.4, 18.9 and 12.2.

EXAMPLE 2

N-Methylamide of monic acid A

A solution of monic acid (0.344 g; 1 mM) in dry THF (10 ml) was cooled to $-10°$ C. Triethylamine (0.140 ml; 1 mM) was added, followed by isobutyl chloroformate (0.133 ml; 1 mM). The mixture was stirred at $-10°$ C. for 10 minutes. A 1% w/v solution of methylamine in water (3.10 ml; 1 mM) was added at once and the mixture stirred at room temperature for 1½ hours. The THF was removed in vacuo and water was added (5 ml). The aqueous mixture was extracted with EtOAc but the product remained in the aqueous layer. The latter was evaporated to a gum (0.451 g), which was dissolved in MeOH and purified on three 20×20×0.2 cm preparative silica plates and eluted with CHCl$_3$/MeOH 5:1. The major band corresponding to the amide was removed and isolated as a gum, which solidified to a foam (0.126 g). Tlc revealed one spot Rf=0.6 in CHCl$_3$/MeOH 3:1 and one component by hplc $[\alpha]_D^{20}-16.3°$ (c 1.0, EtOH), $\lambda_{max}$ (EtOH) 221 nm ($\epsilon_m$ 13,100), $\nu_{max}$ (KBr) 3400, 2960, 2800, 1660, 1630, 1550 cm$^{-1}$, $\delta_H$(d$^6$-DMSO) 7.55 (1H, q, —N$\underline{H}$-Me), 5.58 (1H, s, C=C$\underline{H}$) 2.55 (3H, d, NH—C$\underline{H}_3$), 2.04 (3H, s,

1.05 (3H, d,

and 0.81 (3H, d, C$\underline{H}_3$CH), $\delta_C$ (CD$_3$OD) 170.3 (C-1), 151.8 (C-3), 121.0 (C-2), 76.2 (C-5), 71.6 (C-13), 70.7 (C-7), 70.0 (C-6), 66.3 (C-16), 61.2 (C-11), 56.8 (C-10), 43.7 (C4 and C12), 41.6 (C-8), 33.0 (C-9), 26.0 (C$\underline{H}_3$—N), 20.4 (C-14), 18.8 (C-15) and 12.3 (C-17).

EXAMPLE 3

Methoxycarbonylmethylamide of monic acid A

Monic acid (0.688 g; 2 mM) was dissolved in dry distilled THF (30 ml) and stirred at $-15°$ C. for 20 minutes with triethylamine (0.202 g; 280 μl; 2 mM) and isobutylchloroformate (0.273 g; 260 μl; 2 mM). A solution of glycine methyl ester hydrochloride (0.251 g; 2 mm) and triethylamine (0.202 g; 280 μl; 2 mM) in dichloromethane (20 ml) was then added and the reaction mixture stirred at 0° C. for 30 minutes and room temperature for 2 hours. The solvent was then removed at reduced pressure and the residue partitioned between ethyl acetate and dilute citric acid solution. The organic layer was washed with sodium bicarbonate solution, saturated brine and dried over anhydrous MgSO$_4$. However, tlc revealed that some of the product had dissolved in the citric acid solution. This solution was therefore adjusted to pH 6.0, evaporated to dryness and the residue digested in ethanol. The ethanol filtrate and ethyl acetate solution were combined and evaporated to dryness. The crude amide was then purified by preparative tlc, eluting the silica plates with 3:1 chloroform/methanol. The major band gave the pure (by hplc and tlc) methyl N-monylglycinate as a white foam (0.420 g; 51%), $[\alpha]_D^{20}=-17.6°$ (c 1.0, CH$_3$OH). $\lambda_{max}$ (EtOH) 223 nm ($\epsilon_m$ 13,600), $\nu_{max}$ (KBr) 3400, 1740, 1660 and 1630 cm$^{-1}$, $\delta_H$ (CD$_3$OD) 5.79 (1H, s, C$\underline{H}$=C), 3.91 (2H, s, C$\underline{H}_2$CO$_2$), 3.69 (3H, s, CO$_2$C$\underline{H}_3$), 2.11 (3H, s,

1.18 (3H, d, J=7.0 Hz, C$\underline{H}_3$-14), 0.92 (3H, d, J=7.0 Hz, C$\underline{H}_3$-17), $\delta_C$ (CD$_3$OD) 172.0, 169.7, 153.3, 120.4, 76.1, 71.5, 70.6, 69.9, 66.2, 61.2, 56.7, 52.5, 43.6, 41.6, 41.4, 32.9, 20.3, 19.0, 12.2, m/e 227 (10%), no. M$^+$.

EXAMPLE 4

Dimethylamide of monic acid A

Diethyl chlorophosphate (1.035 g; 6 mM) was added to a solution of monic acid A (2.064 g; 6 mM) and triethylamine (0.840 ml; 6 mM) in dry THF (75 ml). This solution was stirred at room temperature for 3 hours, under a nitrogen atmosphere. A solution of dimethylamine (2.16 ml; ~12 mM; 25% w/v in H$_2$O) was then added and the reaction mixture stirred for a further 16 hours at room temperature. The solvent was then removed at reduced pressure and the residue digested in methanol. Filtration and removal of the solvent at reduced pressure afforded the crude amide as a yellow oil. The product was purified by column chromatography over silica gel (Type 60; 30 g). Elution with 5% methanol/chloroform gave the pure dimethylamide of monic acid A as a colourless oil. (0.814 g; 37%), $[\alpha]_D^{20}-4.32°$ (c 1.0 CH$_3$OH); $\lambda_{max}$ (EtOH) 216 nm ($\epsilon_m$ 8,070); $\nu_{max}$ (CHBr$_3$) 3400, 1645, 1600 cm$^{-1}$, $\delta_H$ (CDCl$_3$) 5.84 (1H, s, C$\underline{H}$=C), 3.02 and 2.96 (two s; N—C$\underline{H}_3$ protons), 1.89 (3H, s, C$\underline{H}_3$-15), 1.21 (3H, d, J 6.5 Hz, C$\underline{H}_3$-14), 0.93 (3H, d, J 7.0 Hz, C$\underline{H}_3$-17); $\delta_C$ (CDCl$_3$) 169.7, 146.2, 120.1, 75.4, 71.0, 69.3, 65.8, 61.3, 56.1, 43.0, 42.0, 40.2, 38.3, 35.2, 32.2, 21.0, 19.5, 12.8. (Found: m/e 156.1055 C$_8$H$_{14}$NO$_2$ requires 156.1024) (Found: m/e 127.0987. C$_7$H$_{13}$NO requires 127.0997).

EXAMPLE 5

5-Ethoxycarbonylpentylamide of monic acid A

To a solution of monic acid (2.064 g; 6 mM) and triethylamine (0.840 ml; 6 mM) in dry THF (50 ml) was added a solution of diethyl phosphorochloridate (1.035 g; 6 mM) in dry THF (20 ml). The solution was stirred at room temperature for 3 hours under an argon atmosphere. A solution of triethylamine (0.840 ml; 6 mM) and 5-ethoxycarbonylpentylamine hydrochloride (1.173 g; 6 mM) in aqueous THF (25 ml) was then added and the reaction mixture stirred at room temperature for 16 hours. The solvent was then removed at reduced pressure and the residue partitioned between ethyl acetate and sodium bicarbonate solution. The organic layer was washed with water, saturated brine and dried over MgSO$_4$. Removal of the solvent at reduced pressure afforded the crude amide as a pale yellow oil (1.663 g). This oil was purified by preparative tlc on four 20×20×0.2 cm silica plated, eluting with 12% methanol/chloroform. The major band yielded the pure 5-ethoxycarbonylpentylamide of monic acid as a colourless oil (1.07 g; 37%), $[\alpha]_D^{20}$ −15.85° (c, 1.0 CH$_3$OH), $\lambda_{max}$ (EtOH) 223 nm ($\epsilon_m$ 14,600), $\nu_{max}$ (CHBr$_3$) 3375, 1720, 1660 and 1630 cm$^{-1}$, $\delta_H$(CD$_3$OD) 7.62 (broad resonance, NH); 5.69 (1H, s, CH=C) 4.06 (2H, q, CO$_2$CH$_2$). 2.10 (3H, s, CH$_3$-15); 1.22 (t+d, 6H, CO$_2$CH$_2$CH$_3$+CH-14); 0.93 (3H, d, J=6.0 Hz, CH$_3$-17), $\delta_c$ (CD$_3$OD) 175.1, 169.3, 151.5, 121.1, 76.1, 71.4, 70.5, 69.9, 66.1, 61.2, 61.1, 56.6, 43.5, 41.3, 39.7, 34.8, 32.8, 30.0, 27.3, 25.5, 20.3, 18.8, 14.5 and 12.2.

EXAMPLE 6

Morpholinyl amide of monic acid A

Diethyl chlorophosphate (1.035 g; 6 mM) was added to a solution of monic acid A (2.064 g; 6 mM) and triethylamine (0.840 ml; 6 mM) in dry THF (50 ml). This solution was stirred at room temperature for 3 hours, under a nitrogen atmosphere. A solution of morpholine (0.522 g; 6 mM) in dry THF (10 ml) was then added and the reaction mixture stirred for a further 16 hours at room temperature. The solvent was then removed at reduced pressure and the residue digested in methanol. Filtration and removal of the solvent at reduced pressure afforded the crude amide as a white solid. The product was purified by column chromatography over silica gel (Type 60; 30 g). Elution with 5% methanol/chloroform gave the pure morpholinyl amide of monic acid A as a colourless oil. (0.538 g; 26%); $[\alpha]_D^{20}$ −3.05° (c, 1.0 CH$_3$OH), $\lambda_{max}$ (EtOH) 219 nm ($\epsilon_m$ 7,530), $\nu_{max}$ (CHBr$_3$) 3400, 1645, 1600 cm$^{-1}$, $\delta_H$(CDCl$_3$) 5.73 (1H, s, CH=C), 3.60 (broad s, methylene protons), 1.85 (3H, s, CH$_3$-15), 1.18 (3H, d, J 6.5 Hz, CH$_3$-14), 0.90 (3H, d, J 7.0 Hz, CH$_3$-17), $\delta_C$ (CDCl$_3$) 167.9, 146.0, 119.2, 74.9, 70.7, 68.9, 66.9, 65.4, 60.9, 55.6, 42.7, 41.5, 39.8, 31.8, 20.7, 19.2, 12.5; m/e (relative intensity) 413 (M+ 2.5%), 188 (50), 182 (20), 170 (35), 154 (50), 83 (100).

EXAMPLE 7

8-Methoxycarbonyloctylamide of monic acid A

Diethyl chlorophosphate (0.507 g; 2.94 mM) was added to a solution of monic acid A (0.982 g; 2.94 mM) and triethylamine (0.412 ml; 2.94 mM) in dry tetrahydrofuran (50 ml). This solution was stirred at room temperature for three hours, under a nitrogen atmosphere. A solution of 8-methoxycarbonyloctylammonium chloride (0.65 g; 2.94 mM) and triethylamine (0.412 ml; 2.94 mM) in aqueous tetrahydrofuran (10 ml) was then added and the reaction mixture stirred for a further sixteen hours at room temperature. The solvent was then removed at reduced pressure and the residue partitioned between ethyl acetate and saturated sodium bicarbonate solution. The organic layer was washed with brine, dried over anhydrous magnesium sulphate and the solvent removed to yield the crude amide as a yellow oil. The product was purified by preparative thin layer chromatography on four 20×20×0.2 cm silica plates, eluting with 12% methanol/chloroform. The major band afforded the pure 8-methoxycarbonyloctylamide of monic acid A as a colourless oil. (0.610 g; 40%), $[\alpha]_D^{20}$ −0.74° (c, 1.0 CHCl$_3$), $\lambda_{max}$ (EtOH) 223 nm ($\epsilon_m$ 14,130); $\nu_{max}$ (CHBr$_3$) 3350, 1780, 1660 and 1630 cm$^{-1}$; $\delta_H$ (CDCl$_3$) 5.93 (1H, broad t, (NH), 5.62 (1H, s, CH=C), 3.65 (3H, s, CO$_2$CH$_3$), 2.13 (3H, s, CH$_3$-15), 1.30 (s, methylene envelope), 1.20 (3H, d, J 6.0 Hz, CH$_3$-14), 0.92 (3H, d, J 7.0 Hz, CH$_3$-17); $\delta_C$ (CDCl$_3$) 174.4, 167.6, 150.3, 120.4, 75.1, 70.8, 70.5, 68.9, 65.5, 61.0, 55.7, 51.5, 42.7, 39.8, 39.4, 34.1, 31.8, 29.6, 29.1, 27.0, 24.9, 20.8, 18.7, 12.6, m/e 513 (M+) 482, 366, 269, 227, 188, 172, 156, 11, 83.

EXAMPLE 8

Allylamide of monic acid A

Diethyl chlorophosphate (1.035 g; 6 mM) was added to a solution of monic acid A (2.064 g; 6 mM) and triethylamine (0.840 ml; 6 mM) in dry tetrahydrofuran (100 ml). This solution was stirred at room temperature for three hours, under a nitrogen atmosphere. Allylamine (0.684 g; 12 mM) was then added and the reaction mixture stirred for a further sixteen hours at room temperature. The solvent was then removed at reduced pressure and the residue partitioned between ethyl acetate and sodium bicarbonate solution. The organic layer was washed with brine, dried over anhydrous magnesium sulphate and the solvent removed at reduced pressure to yield the crude amide. The product was purified by silica gel column chromatography (Type 60; 25 g), eluting with 5% methanol chloroform and preparative thin layer chromatography on two 20×20×0.2 cm silica plates, eluting with 9:1 chloroform/methanol. The major band gave the pure allylamide of monic acid A as a colourless oil, (0.380 mg; 17%), $[\alpha]_D^{20}$ −1.1° (c, 1.0 CHCl$_3$); $\lambda_{max}$(EtOH) 222 nm ($\epsilon_m$ 15,100); $\nu_{max}$(CHBr$_3$) 3350, 1660, 1630 cm$^{-1}$; $\delta_H$ (CDCl$_3$) 5.80 (1H, m, CH=CH$_2$), 5.69 (1H, s, CH-2), 5.15 (2H, m, CH=CH$_2$), 2.17 (3H, s, CH$_3$-15), 1.23 (3H, d, J 6.0 Hz, CH$_3$-14); 0.93 (3H, d, J 7.5 Hz, CH$_3$-17), $\delta_C$ (CDCl$_3$) 167.5, 151.2, 134.4, 120.1, 116.4, 75.1, 71.0, 70.5, 69.0, 65.4, 61.1, 55.8, 42.8, 41.8, 39.8, 20.8, 18.9, and 12.6; m/e 383 (M+), 368, 365, 339, 298, 238, 227, 168, 139, 111, 83 (100%).

EXAMPLE 9

5-Methoxycarbonylpentylamide of monic acid A

Diethyl chlorophosphate (0.7 ml; 5 mM) was added to a solution of monic acid A (1.72 g; 5 mM) and triethylamine (0.7 ml; 5 mM) in dry THF (40 ml). This solution was stirred at room temperature for 3 hours. A solution of 5-methoxycarbonylpentylamine hydrochloride (0.91 g; 5 mM) and triethylamine (0.7 ml) in 50% aqueous THF (40 ml) was then added and the reaction mixture stirred at room temperature for a further 16 hours. The solvent was then removed at reduced pressure and the residue partitioned between ethyl acetate and water. The aqueous phase was further extracted with ethyl acetate and the organic fractions bulked and washed with sodium bicarbonate solution and brine, dried (MgSO$_4$), and evaporated in vacuo to give an oil. Separation on a silica column (16 g, type 60) eluting with 2% MeOH/CHCl$_3$, gave the pure product as an oil (0.288 g; 12%); $[\alpha]_D^{20}$ 1.62° (c, 1.0, CHCl$_3$); $\nu_{max}$ (CHCl$_3$) 3440, 3000, 2940, 1730, 1660, 1630 cm$^{-1}$; $\lambda_{max}$ 221 nm ($\epsilon_m$ 13,300); $\delta_H$ (CDCl$_3$) 6.11 (1H, t, NH), 5.63 (1H, s, C2-H), 3.63 (3H, s, CO$_2$CH$_3$), 2.11 (3H, s, C15-CH$_3$), 1.19 (3H, s, C14-CH$_3$), 0.91 (3H, s, C17-CH$_3$); $\delta_C$ (CDCl$_3$) 174.2 (C1), 167.5 (C1), 150.3 (C3), 120.5 (C2), 75.1 (C5), 71.2 (C13), 70.6 (C7), 69.0 (C6), 65.4 (C16), 61.2 (C11), 55.7 (C10), 51.6 (OCH$_3$), 42.8 (C4, C12), 39.7 (C8), 39.1 (C6'), 33.9 (C2'), 31.8 (C9), 29.3 (C4'), 26.5 (C5'), 24.6 (C3'), 20.9 (C14), 18.8 (C15), 12.7 (C17); m/e (relative intensity) 471 (M+, 1.8), 227 (100), 146 (58), 111 (70), 109 (58); (Found: M+ 471.2831, $C_{24}H_{41}NO_8$ requires 471.2833).

EXAMPLE 10

2-Methoxycarbonylethylamide of monic acid A

Monic acid A (1.72 g; 5 mM) was dissolved in THF (40 ml) with triethylamine (0.7 ml; 5 mM), diethyl phosphorochloridate added (0.85 g; 5 mM), and stirred under an argon atmosphere for 3 hours. The precipitated triethylamine hydrochloride was filtered off and a solution of β-alanine methyl ester hydrochloride (0.7 g; 5 mM) in aqueous THF (50%; 40 ml) and triethylamine (0.7 ml) was added and the reaction was stirred overnight at room temperature. After evaporation to dryness, the residue was dissolved in water (20 ml), saturated with brine and extracted with ethyl acetate (5×40 ml). The combined ethyl acetate extracts were dried (MgSO₄) and evaporated to dryness to give an oil. Separation on a silica column (type 60, 30 g) gave the product as an oil (0.335 g; 16%), $\nu_{max}$ (CDCl₃) 3420, 3000, 1730, 1665, 1635 cm⁻¹; $\lambda_{max}$ (EtOH) 222 nm ($\epsilon_m$ 14,790); $\delta_H$ (CDCl₃) 6.47 (1H, t, NH), 5.65 (1H, s, C2-H), 3.67 (3H, s, —CO₂CH₃), 2.11 (3H, s, C15-CH₃), 1.20 (3H, d, C14-CH₃), 0.91 (3H, d, C17-CH₃), $\delta_C$ (CDCl₃) 173.0 (C1'), 167.6 (C1), 151.3 (C3), 120.0 (C2), 75.1 (C5), 70.8 (C13), 70.5 (C7), 69.0 (C6), 65.4 (C16), 60.9 (C11), 55.7 (C10), 51.8 (OMe), 42.7 (C4, C12), 39.8 (C8), 34.9 (C3'), 34.0 (C2'), 31.8 (C9), 20.7 (C7), 18.8 (C15), 12.5 (C17).

BIOLOGICAL DATA (a) Human bacteria

Table 1 shows the MIC values (μg/ml) of the compounds of Examples 1–9 against a number of organisms important in human infections obtained by serial dilution in nutrient agar containing 5% 'chocolated' horse blood.

TABLE 1

| | M.I.C. | | | | | | | | |
|---|---|---|---|---|---|---|---|---|---|
| | Compound of Example No: | | | | | | | | |
| Organism | 1 | 2 | 3 | 4 | 5 | 6 | 7 | 8 | 9 |
| Pasteurella multocida 1633 | 10 | 2.5 | 12.5 | 2.5 | — | 1.0 | 1.0 | 0.05 | 0.2 |
| Haemophilus influenzae Q1 | 5.0 | 0.2 | 1.2 | 2.5 | 0.05 | 0.2 | 0.5 | >100 | 0.2 |
| Haemophilus influenzae Wy21 | 10 | — | 1.2 | 2.5 | 0.5 | 0.5 | 0.5 | — | — |
| Neisseria flavescens 8263 | 2.5 | 1.0 | 25 | — | — | — | — | — | — |
| Neisseria catarrhalis 1502 | — | — | — | 2.5 | 0.05 | 5.0 | 0.1 | 100 | <0.02 |
| Bacillus subtilis 6633 | 100 | 10 | 25 | 25 | 10 | 10 | 2.5 | 2.5 | 10 |
| Staph. aureus Oxford | 50 | 2.5 | 25 | 5.0 | 25 | 10 | 10 | 2.5 | 25 |
| Staph. aureus Russell | 100 | 25 | 125 | 25 | 50 | 50 | 25 | 100 | 100 |
| Strep. pneumoniae CN33 | 100 | 25 | 25 | 50 | 1.0 | 10 | — | 5.0 | 2.5 |

(b) Veterinary bacteria

Table 2 shows the MIC values (μg/ml) of some of the compounds of the Examples against a number of organisms important in veterinary infections.

TABLE 2

| | M.I.C. | | | | | | | | |
|---|---|---|---|---|---|---|---|---|---|
| | Compound of Example No: | | | | | | | | |
| Organism | 1 | 3 | 4 | 5 | 6 | 7 | 8 | 9 | 10 |
| Bord. bronchiseptica BO9 | 40 | 5 | 40 | 23 | 20 | 2.0 | 1.25 | 10 | 20 |
| Past. multocida PAI | 40 | 10 | 5 | 0.35 | 0.625 | 1.0 | 1.25 | 10 | 0.625 |
| Past. haemolytica PA5 | 40 | 5 | 40 | 11 | 20 | 8.0 | 0.625 | 10 | 5 |
| Staph. aureus B4 | >80 | 40 | 20 | 11 | 20 | 4.0 | 5 | 20 | 80 |
| Staph. aureus 152 | >80 | >80 | >80 | 45 | >80 | 8.0 | 20 | 20 | — |
| Strep. uberis SPU 1 | 20 | 5 | 20 | 0.35 | 2.5 | 0.125 | 0.625 | 0.625 | 2.5 |
| Strep. dysgalactiae SPD 1 | 20 | 1.25 | 20 | 0.7 | 2.5 | 0.0625 | 0.156 | 0.312 | 20 |

(c) Anti-mycoplasmal activity

Tables 3 and 4 show the in vitro MIC values (μg/ml) of the compounds of Examples 1 to 9 against a number of mycoplasma organisms, determined in Friis' broth using the microtiter method.

TABLE 3

| | M.I.C. | | | | |
|---|---|---|---|---|---|
| | Compound of Example No: | | | | |
| Organism | 1 | 2 | 3 | 4 | 5 |
| M. suipneumoniae Str. 11 | — | — | — | 10 | 1.25 |
| M. suipneumoniae J2206/183b | 7.8 | <0.5 | 7.8 | >10 | 2.5 |
| M. dispar H225 | — | — | — | 5.0 | 0.312 |
| M. dispar NCTC 10125 | 1.9 | <0.5 | <0.5 | 2.5 | 0.156 |
| M. pneumoniae 427a | 250 | 125 | 250 | >10 | >10 |
| M. pneumoniae ATCC 15492 | — | — | — | >10 | 10 |
| M. fermentans MWKL4 | 15.6 | 7.8 | <0.5 | 1.25 | 0.039 |
| M. pulmonis JB | 15.6 | 1.0 | 62.5 | 5.0 | <0.02 |

TABLE 4

| | M.I.C. | | | |
|---|---|---|---|---|
| | Compound of Example No: | | | |
| Organism | 6 | 7 | 8 | 9 |
| M. suipneumoniae Str. 11 | 2.5 | 1.25 | 0.625 | 0.625 |
| M. suipneumoniae J2206/183b | 10 | 10 | 1.25 | 1.25 |
| M. dispar H225 | 1.25 | 0.156 | 0.078 | 0.312 |
| M. dispar NCTC 10125 | 2.5 | 0.156 | 0.078 | 0.312 |
| M. pneumoniae 427a | >10 | 10 | 10 | 5.0 |
| M. pneumoniae ATCC 15492 | >10 | 10 | — | — |
| M. fermentans MWKL4 | 0.625 | <0.02 | 0.039 | 0.039 |
| M. pulmonis JB | 0.156 | <0.02 | 0.039 | 0.039 |

(d) Mouse blood levels

The blood levels of the 5-ethoxycarbonylpentyl amide of monic acid A were measured after subcutaneous dosing to male albino mice. The results are shown in table 5 and demonstrate that blood levels of the amide are higher and more prolongued than those obtained after subcutaneous dosing of pseudomonic acid.

Species: Albino male mice 18–22 g CS1 strain.
Routes: Subcutaneous and oral.
Dose: 50 mg/kg. This compound was supplied as an oil. It was administered as a solution in 10% DMF v/v in PBS or water.
Assay: Neisseria catarrhalis, immediate assay of samples.

TABLE 5

| Compound | Concentration (μg/ml) minutes after dosing (means of 5 experiments) | | | | | Half-life (minutes) |
|---|---|---|---|---|---|---|
| | 5 | 10 | 20 | 30 | 60 | |
| Compound of Example 5 | 22.1 | 22.6 | 16.1 | 9.1 | <4.0 | 15 |
| Pseudomonic Acid | 8.2 | 3.7 | 1.1 | 0.62 | <0.5 | 5 |

I claim:

1. A carboxylic acid amide of formula:

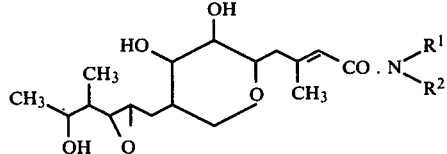

wherein $R^1$ is hydrogen or alkyl of 1 to 6 carbon atoms and $R^2$ is hydrogen, alkyl of 1 to 4 carbon atoms, alkenyl of 2 to 8 carbon atoms, or $-(CH_2)_n COOR^3$ wherein n is an integer from 1 to 20 and $R^3$ is hydrogen or a pharmaceutically acceptable salt-forming ion or alkyl of 1 to 6 carbon atoms or $R^1$ and $R^2$, together with the nitrogen atom to which they are attached, are pyrrolidinyl, piperidinyl or morpholino.

2. An amide according to claim 1 wherein $R^1$ is hydrogen and $R^2$ is $-(CH_2)_n COOR^3$ wherein n is an integer from 1 to 10 and $R^3$ is as therein defined.

3. An amide according to claim 1 wherein $R^1$ is hydrogen and $R^2$ is the residue of a naturally occurring amino acid of the formula $R^2 NH_2$.

4. A compound according to claim 1 selected from the group consisting of monic acid A amide; monic acid A N-methylamide; monic acid A methoxycarbonylmethylamide; monic acid A 5-ethoxycarbonylpentylamide; monic acid A N-morpholinylamide; monic acid A 8-methoxycarbonyloctylamide; monic acid A allylamide; monic acid A 5-methoxycarbonylpentylamide; and monic acid A methoxycarbonylethylamide.

5. A pharmaceutical or veterinary composition comprising an antibacterially effective amount of an amide according to claim 1 in combination with a pharmaceutically or veterinary acceptable carrier or excipient.

6. The method of treating bacterial and mycoplasma-induced infections in humans and veterinary animals which comprises administering thereto an effective amount of a compound according to claim 1.

* * * * *